United States Patent [19]

Vavere

[11] Patent Number: 4,547,614
[45] Date of Patent: Oct. 15, 1985

[54] PROCESS FOR THE PREPARATION OF CONJUGATED DIENES BY DEHYDRATION OF ALDEHYDES

[75] Inventor: Atis Vavere, St. Louis, Mo.
[73] Assignee: Monsanto Company, St. Louis, Mo.
[21] Appl. No.: 534,023
[22] Filed: Sep. 20, 1983
[51] Int. Cl.[4] .............................................. C07C 1/20
[52] U.S. Cl. ................................................... 585/606
[58] Field of Search ....................................... 585/606

[56] References Cited

U.S. PATENT DOCUMENTS 1,033,180  7/1912  Kyriakides et al. ................. 585/606
1,033,327  7/1912  Kyriakides et al. ................. 585/606

FOREIGN PATENT DOCUMENTS 1385348  2/1975  United Kingdom .
721116  3/1980  U.S.S.R. .

OTHER PUBLICATIONS

Bol'shakov et al., Prom-st. Sint. Kauch., 1980, (8), 2–4.

Primary Examiner—Curtis R. Davis
Attorney, Agent, or Firm—Dennis R. Hoerner, Jr.; James W. Williams, Jr.

[57] ABSTRACT

An improved process for the preparation of conjugated dienes, particularly isoprene, from the corresponding aliphatic aldehyde using an acidic dehydration catalyst is disclosed. The present invention embraces the surprising discovery that catalyst activity and selectivity, particularly for boron phosphate catalyst, can be substantially prolonged by reducing the aldehyde liquid hourly space velocity to less than about 3.0 hr$^{-1}$ and preferably to less than about 1.0 hr$^{-1}$.

6 Claims, No Drawings

PROCESS FOR THE PREPARATION OF CONJUGATED DIENES BY DEHYDRATION OF ALDEHYDES

BACKGROUND OF THE INVENTION

The present invention relates to the preparation of conjugated dienes by dehydration of aliphatic aldehydes and more particularly to the dehydration of 2-methylbutanal to obtain isoprene.

It is known that conjugated dienes can be obtained from the corresponding aliphatic aldehyde having the same number of carbon atoms by contacting the aldehyde with an acidic dehydration catalyst. Examples of suitable acid dehydration catalysts include inorganic acids such as phosphoric acid, boric acid, silicic acid and titanic acid. Other suitable acidic dehydration catalysts include the salts of the above-described acids and acid anhydrides having a latent acid function. While use of the above-described catalysts to dehydrate aldehydes to conjugated dienes is known, embodiments of this process reported heretofore have been substantially impeded by catalyst deactivation with attendant loss of selectivity after as short a period as thirty minutes, see British Pat. No. 1,385,348.

It is therefore the overall object of the present invention to provide an improved process for the dehydration of aliphatic aldehydes to obtain the corresponding conjugated diene.

Accordingly, it is an object of the present invention to provide an improved process having prolonged catalyst activity.

It is yet another object of the present invention to provide an improved process having sustained catalyst selectivity versus reaction time.

These and other objects, features and advantages of the present invention will be evident to those skilled in the art from the following description.

SUMMARY OF THE INVENTION

The present invention provides an improved process for the preparation of conjugated dienes, particularly isoprene, by the dehydration of the corresponding aliphatic aldehyde. While conventional acidic dehydration catalysts are suitable for use in the present invention, boron phosphate catalyst is preferred. The process is carried out at a temperature between 250° C. and 500° C. and preferably between about 300° C. and 400° C. The process can be carried out at reduced, normal or elevated pressure in the presence or absence of a non-interfering carrier gas. The present process embraces the surprising discovery that catalyst activity and selectivity can be substantially prolonged by reducing the liquid hourly space velocity of the aldehyde reactant to less than 3.0 hr$^{-1}$ and preferably to less than about 1.0 hr$^{-1}$.

DETAILED DESCRIPTION OF THE INVENTION

The present invention provides an improved process for the preparation of conjugated dienes from the corresponding aliphatic aldehyde having the same number of carbon atoms by contacting the aldehyde reactant with an acidic dehydration catalyst, for example, see British Pat. No. 1,385,348, the disclosure of which is hereby specifically incorporated by reference. The present process embraces the surprising discovery that catalyst activity and selectivity can be substantially prolonged by reducing the liquid hourly space velocity of aldehyde to less than 3.0 hr$^{-1}$ and preferably less than about 1.0 hr$^{-1}$. By liquid hourly space velocity is meant the liquid volume of aldehyde reactant supplied per hour divided by the volume of catalyst used.

Dehydration of aldehydes to obtain conjugated dienes by the process of the present invention can be carried out at reduced, normal or elevated pressures. The process is generally carried out at a temperature between 250° C. and 500° C. and preferably between about 300° C. and 400° C. The liquid hourly space velocity of the process is easily controlled by regulating the flow rate of aldehyde reactant into the reactor wherein the aldehyde contacts the acidic dehydration catalyst. While the process is capable of operating with or without a carrier gas, inert gases such as helium, nitrogen or water vapor are preferred since the presence of the carrier gas affords an additional means of controlling the residence time of the aldehyde reactant in the reactor.

Suitable catalysts for use in the process of the present invention are acidic dehydration catalysts including inorganic acids such as phosphoric acid, boric acid, silicic acid and titanic acid. Salts of the above-described acids and acid anhydrides having a latent acid function are also suitable. The catalysts can be either unsupported or supported on such materials as silica, titania and alumina. Catalysts shape can be granular, cylindrical or spherical. Boron phosphate catalyst is preferred since both aldehyde conversion and diene selectivity are optimized using this material.

Both fixed-bed and fluidized-bed reactor systems are capable of use in the process of the present invention. It should be recognized that fluidized-bed reactors are most useful in carrying out exothermic reactions since heat removal is easily accomplished by cooling the catalyst. However, since the dehydration process is endothermic, the fluidized-bed design affords no apparent advantage over the fixed-bed design.

For conciseness, the present invention will be further described in the following examples with reference to the preparation of isoprene by the dehydration of 2-methylbutanal. The following examples are included to better illustrate the practice of the present invention. It should be understood that these examples are included for illustrative purposes only and are not, in any way, intended to limit the scope of the present invention. Unless otherwise noted, all percentages are by weight and all temperatures are in degrees centigrade.

EXAMPLE 1

A solid boron phosphate catalyst (BPO$_4$) having a boron to phosphate ratio of essentially 1.0 was prepared by bureting 55.3 ml of an 85 wt. % phosphoric acid solution into a 53.3 gram sample of 99.8 wt % pure boric acid with attendant manual stirring of the mixture. The material was dried over a steam bath for about 3 hours with nitrogen gas purging over it. The resulting solid was calcined in a ceramic dish at 600° C. for 2 hours and cooled to 150° C. overnight.

A 5.0 cm$^3$ sample (3.3 gm) of the above-described boron phosphate catalyst was introduced into a fixed-bed vapor phase reactor. The feed stream to the reactor consisted of 6.4 mole % 2-methylbutanal and 93.6 mole % helium. Feed stream flow rates were adjusted to obtain a 2-methylbutanal liquid hourly space velocity of 0.3 hr$^{-1}$. The reaction was carried out at a temperature of 350° C. and a pressure of about 15 pounds per square inch gauge.

Conversion of 2-methylbutanal and the yield of isoprene was determined by conventional gas chromatographic analysis of the reactor effluent. The above-described conditions yielded the following results.

| Time, hrs. | 2-methylbutanal conversion, mole % | Isoprene Selectivity | Isoprene Yield, mole % |
|---|---|---|---|
| 0 | 87.8 | 68.2 | 60.0 |
| 0.17 | 87.0 | 72.6 | 63.2 |
| 0.35 | 87.1 | 73.7 | 64.2 |
| 0.52 | 86.2 | 75.3 | 64.9 |
| 0.70 | 86.0 | 76.4 | 65.7 |
| 0.88 | 85.7 | 77.6 | 66.5 |
| 1.05 | 84.3 | 78.3 | 66.0 |
| 1.23 | 85.6 | 79.4 | 68.0 |
| 1.58 | 85.9 | 80.7 | 69.3 |
| 1.75 | 86.0 | 81.0 | 69.7 |
| 1.93 | 86.1 | 82.0 | 70.6 |

EXAMPLE 2

The same experiment was conducted as described in Example 1 except that the 2-methylbutanal feed stream consisted of 12.5 mole % 2-methylbutanal, 68.8 mole % water vapor and 18.7 mole % nitrogen. The flow rate of the feed stream was regulated to obtain a 2-methylbutanal liquid hourly space velocity of 0.7 hr$^{-1}$.

Conversion of 2-methylbutanal and the yield of isoprene were determined by conventional gas chromatographic analysis of the reactor effluent. The above-described conditions yielded the following results.

| Time, hrs. | 2-methylbutanal conversion, mole % | Isoprene Selectivity | Isoprene Yield, mole % |
|---|---|---|---|
| 0 | 82 | 90 | 73.8 |
| 0.18 | 79 | 89 | 70.3 |
| 0.55 | 73 | 92 | 67.2 |
| 0.91 | 67 | 92 | 61.6 |
| 1.28 | 59 | 94 | 55.5 |
| 1.65 | 52 | 95 | 49.4 |
| 2.00 | 47 | 95 | 44.7 |
| 2.35 | 40 | 98 | 39.2 |

EXAMPLE 3

The same experiment was conducted as described in Example 1 except that the 2-methylbutanal feed stream consisted of 14.8 mole % 2-methylbutanal, 61.7 mole % helium and 23.5 mole % nitrogen. The flow rate of the feed stream was regulated to obtain a 2-methylbutanal liquid hourly space velocity of 0.7 hr$^{-1}$.

Conversion of 2-methylbutanal and the yield of isoprene were determined by conventional gas chromatographic analysis of the reactor effluent. The above-described conditions yielded the following results.

| Time, hrs. | 2-methylbutanal conversion, mole % | Isoprene Selectivity | Isoprene Yield, mole % |
|---|---|---|---|
| 0 | 85 | 80 | 68.0 |
| 0.18 | 85 | 84 | 71.4 |
| 0.55 | 84 | 88 | 73.9 |
| 0.73 | 82 | 89 | 73.0 |
| 0.92 | 79 | 90 | 71.0 |
| 1.28 | 71 | 90 | 63.9 |
| 1.47 | 66 | 92 | 60.7 |

Embodiments of the general process of the present invention reported heretofore have generally utilized an aldehyde liquid hourly space velocity in the range of 3.5 hr$^{-1}$ to 5.0 hr$^{-1}$. As a consequence prior attempts to utilize this process have been substantially impeded by rapid deactivation and loss of selectivity of the acidic dehydration catalyst within as short a period as thirty minutes, see British Pat. No. 1,385,348. The present invention embraces the surprising discovery that the activity of the acidic dehydration catalyst, particularly boron phosphate catalyst, could be substantially prolonged with no attendant loss in catalyst selectivity by reducing the aldehyde liquid hourly space velocity of the aldehyde reactant below levels reported heretofore. The aldehyde reactant is supplied at a rate corresponding to a liquid hourly space velocity of less than about 3.0 hr$^{-1}$ and preferably less than about 1.0 hr$^{-1}$.

I claim:

1. In a process for the preparation of conjugated dienes by the dehydration of the corresponding aliphatic aldehyde in the presence of an acidic dehydration catalyst, the improvement comprising controlling the aldehyde reactant feed rate so that the aldehyde liquid hourly space velocity is less than about 1.0 hr$^{-1}$.

2. The process of claim 1 in which the reaction is carried out at a temperature between about 300° C. and 400° C.

3. In a process for the preparation of conjugated dienes by the dehydration of the corresponding aliphatic aldehyde in the presence of a boron phosphate catalyst, the improvement comprising controlling the aldehyde reactant feed rate so that the aldehyde liquid hourly space velocity is less than about 1.0 hr$^{-1}$.

4. The process of claim 3 in which the reaction is carried out at a temperature between about 300° C. and 400° C.

5. In a process for the preparation of isoprene by the dehydration of 2-methylbutanal in the presence of a boron phosphate catalyst, the improvement comprising controlling the 2-methylbutanal feed rate so that the 2-methylbutanal liquid hourly space velocity is less than about 1.0 hr$^{-1}$.

6. The process of claim 5 in which the reaction is carried out at a temperature between about 300° C. and 400° C.

* * * * *